United States Patent [19]

Abe et al.

[11] Patent Number: 5,024,946

[45] Date of Patent: Jun. 18, 1991

[54] HUMAN MONOCLONAL ANTIBODY TO ANTIGEN OF GASTRIC CANCER AND B-CELL LINE FOR PRODUCING THIS ANTIBODY, METHOD FOR PREPARING THIS B-CELL LINE AND ANTIBODY, ANTIGEN AND METHOD OF PREPARATION OF THIS ANTIGEN

[75] Inventors: Tsutomu Abe, Fuji; Masayuki Fukumoto, Saitama, both of Japan

[73] Assignee: Asahi Kasei Kabushiki Kaisha, Osaka, Japan

[21] Appl. No.: 912,106

[22] Filed: Sep. 29, 1986

[30] Foreign Application Priority Data

Sep. 30, 1985 [JP] Japan .................................. 60-214480
Jun. 4, 1986 [JP] Japan .................................. 61-128016
Aug. 28, 1986 [JP] Japan .................................. 61-200080

[51] Int. Cl.$^5$ .......................... C12N 5/24; C07K 15/28
[52] U.S. Cl. ............................. 435/240.27; 435/240.2; 435/172.2; 435/70.21; 435/948; 530/388; 935/90; 935/93; 935/100; 935/104; 935/107; 935/108; 424/85.8; 436/548
[58] Field of Search ...................... 435/68, 172.2, 240.2, 435/240.27, 948; 530/387, 388; 935/90, 93, 100, 104, 107, 108; 424/85.8; 436/548

[56] References Cited

U.S. PATENT DOCUMENTS 4,464,465  8/1984  Lostrom ................................ 435/68

OTHER PUBLICATIONS

Ochiai et al., "Production and Analysis of Monoclonal Antibody Against Human Gastric Cancer Cell Line", *Proceedings of the Japanese Cancer Association*, The 44th Annual Meeting, Oct. 1985 (Tokyo), p. 132, Presentation No. 419.

Debus, E. et al., "Monoclonal Cytokeratin Antibodies That Distinguish Simple from Stratified Squamous Epithelia: Characterization on Human Tissues", *EMBO J.* 1(12): 1641–1647, 1982.

Abe, T. et al., "Human Monoclonal Antibodies Against Cytokeratin 18 Generated from Patients with Gastric Cancer", *Jpn. J. Cancer Res.*, 80:271–276, Mar. 1989.

Moll, R. et al., "The Catalog of Human Cytokeratins: Patterns of Expression in Normal Epithelia, Tumors and Cultured Cells," *Cell* 31:11–24, Nov. 1982.

Kotaro Koyama et al., *Jpn. J. Cancer Res.*, 81, 967–970, Oct. '90, "Alloimmunization with Cultured Human Stomach Cancer Cell Lines and the Establishments of Human—Human Hybridomas Producing Monoclonal Antibodies".

Ochiai et al., "Proceedings of the Japanese Cancer Assoc.", The 44th Annual Meeting, Oct. 1985, pp. 132, Presentation No. 419.

*Primary Examiner*—Esther L. Kepplinger
*Assistant Examiner*—Paula Hutzell
*Attorney, Agent, or Firm*—Birch, Stewart, Kolasch & Birch

[57] ABSTRACT

The present invention relates to a human B-cell line capable of producing a human monoclonal antibody against an antigen found on gastric cancer cell lines or tissues. The B-cell line is formed by culturing B-cells of a lymph node obtained from a patient with gastric cancer and a HAT sensitive B-cell line. The antigen is also disclosed.

2 Claims, No Drawings

HUMAN MONOCLONAL ANTIBODY TO ANTIGEN OF GASTRIC CANCER AND B-CELL LINE FOR PRODUCING THIS ANTIBODY, METHOD FOR PREPARING THIS B-CELL LINE AND ANTIBODY, ANTIGEN AND METHOD OF PREPARATION OF THIS ANTIGEN

BACKGROUND OF THE INVENTION

1. Field of the Invention

The present invention relates to a novel human B-cell line and more specifically to a human B-cell line for the production of a novel monoclonal antibody to an antigen of human gastric cancer, to the antibody so produced and to the antigen.

2. Description of the Prior Art

The capacity of the human body to produce immunoglobulins has found applications in medicine and industry. The ability of the human auto-antibody production system to distinguish cancer-related antigens from almost all of the normal cells in the human body has found a wide range of applications in the detection and therapy of cancers. In diagnostic applications, radioisotope-coupled immunoglobulins can be used to identify the location of cancer in a patient. On the other hand, in therapeutic applications immunoglobulins can be used for passive immunization or site-directed therapy against cancer. Major stumbling blocks in the wide use of human immunoglobulin therapy have been a limited probability of selecting B-cell clones and instability of the cell cultures which can produce monoclonal antibodies. The cancer-related antigens defined by human auto-antibodies can also be employed in the active immunotherapy of cancer and as therapeutic markers of cancer.

The discovery by Milstein and Kohler of mouse hybridomas capable of secreting specific monoclonal antibodies against predefined antigens ushered a new era in the field of experimental immunology. The clonal selection and immortality of such hybridoma cell lines assure the monoclonality, monospecificity and permanent availability of their antibodies. However, in human clinical applications the use of such mouse antibodies is clearly limited by the fact that they are foreign proteins and would act as antigens.

A popular method for obtaining a human monoclonal antibody is the transformation of B-cells by treating the cells with culture medium from a marmoset cell line which contains Epstein-Barr virus (hereinafter "EBV"). In clinial applications, the antibody obtained by this method is inevitably contaminated with other viruses from the marmoset cell line.

Another method for the transformation of B-cells is disclosed in detail in U.S. Pat. No. 4,464,465 which employs a human B-cell line as the source of EBV.

A. Ochiai et al. [Proceedings of the Japanese Cancer Association, The 44th Annual Meeting October 1985 (TOKYO) pp132] disclosed a new human gastric cancer-related antigen having a molecular weight of about 46 kilodaltons which exists in tissues of gastric cancer, colon cancer, lung cancer and so on, and which further exists in neutrophil leukocytes which are one type of leukocytes or macrophages.

SUMMARY OF THE INVENTION

There has now been discovered a novel human B-cell line which is capable of producing a novel human monoclonal antibody against an antigen found on gastric cancer cell lines or gastric cancer tissues.

Although several antigen-specific antibodies have been obtained by the EBV transformation of B-cells, the human monoclonal antibody of the present invention has not been reported. The accomplishment of the present invention may be attributed mainly to the obtainment of an antibody producing B-cells from a patient with gastric cancer and to the efficient transformation of the B-cells.

It is accordingly an object of this invention to provide a human B-cell line which can produce a monoclonal antibody against an antigen found on or in gastric cancer cell lines.

It is another object of this invention to provide a human monoclonal antibody which can react with gastric cancer cell lines.

It is a further object of this invention to provide an antigen existing in gastric cancer cell lines which can be advantageously used for clinical examination to determine whether a patient suffers from gastric cancer or lung cancer.

Other objects, features and advantages of the present invention will become apparent from the following detailed description.

Essentially, according to the present invention there is provided a human monoclonal antibody produced from a B-cell line, which reacts with a gastric cancer cell line.

The monoclonal antibody of this invention is of class IgM having the lambda light chain, and reacts with gastric cancer cell lines MKN-45, MKN-1 or KATO-III. Furthermore, it reacts with lung cancer cell line PC-10. The monoclonal antibody of this invention, however, does not react with normal human erythrocytes, leukocytes, lymphocytes or monocytes.

In another aspect of the present invention, there is provided a B-cell line which produces the monoclonal antibody.

The B-cell line of this invention was deposited at the European Collection of Animal Cell Cultures/PHLS Center for applied Microbiology and Research Division of Biologies, Porton Down, Salisbury, Wiltshire, United Kingdom on July 10, 1985 and was given Deposit ref 85071031.

In a further aspect of the present invention, there is provided a method for preparing a B-cell line which produces a human monoclonal antibody which reacts with a gastric cancer cell line which comprises the steps of:

i) preparing B-cells of a lymph node obtained from a patient with gastric cancer and a HAT sensitive B-cell line;

ii) culturing the B-cells of a lymph node and the HAT sensitive B-cell line in a HAT medium to produce cultured transformed B-cells;

iii) screening supernatant from said cultured transformed B-cells for the presence of a human monoclonal antibody which reacts with a gastric cancer cell line; and iv) selecting and cloning transformed B-cells producing the desired antibody.

In a still further aspect of the present invention, there is provided a method for preparing a monoclonal antibody which reacts with a gastric cancer cell line which comprises the steps of:

i) preparing B-cells of a lymph node obtained from a patient with gastric cancer and a HAT sensitive B-cell line;

ii) culturing the B-cells of a lymph node and the HAT-sensitive B-cell line in a HAT medium in wells to produce cultured transformed B-cells;

iii) screening supernatant from said cultured transformed B-cells for the presence of a human monoclonal antibody which reacts with a gastric cancer cell line;

iv) selecting and cloning transformed B-cells producing the desired antibody; and v) recovering the antibody from the supernatant of the cloned transformed B-cells.

In a still more further aspect of the present invention, there is provided an antigen which exists in gastric cancer cell lines and has a molecular weight of $45\pm3$ kilodaltons and an isoelectric point of $4.7\pm0.6$.

The antigen of this invention exists in gastric cancer cell lines MKN-45, KATO-III and MKN-1 and it also exists in lung cancer cell line PC-10. The antigen of this invention, however, does not exist in normal human erythrocytes, leukocytes, lymphocytes or monocytes.

In another aspect of this invention, there is provided a method for preparing an antigen which exists in gastric cancer cell lines and has a molecular weight of $45\pm3$ kilodaltons and an isoelectric point of $4.7\pm0.6$ which comprises the steps of:

i) extracting a gastric cancer cell line with a solution containing a nonionic detergent to give an extract solution containing an antigen;

ii) contacting the solution with a gel coupled with a monoclonal antibody produced from a B-cell line, which reacts with a gastric cancer cell line to bind the antigen to the gel; and iii) eluting the adsorbed antigen from the gel.

The adsorbed antigen is preferably eluted from the gel by passing a solution through the gel which inhibits or reverses the formation of an antigen-antibody complex.

In addition, the antigen of this invention can be separated from gastric cancer cell lines by the conventional biochemical separations such as ion-exchange chromatography, gel chromatography and isoelectric-focusing electrophoresis.

The preparation and characterization of the B-cell line, the resultant monoclonal antibody and the cancer-related antigen will be better understood by reference to the following detailed description and Example.

DETAILED DESCRIPTION OF THE INVENTION

I. Mixed Culture Transformation (1) Preparation of antibody producing B-cells The human B-cells which can be employed in the present invention are widely distributed in lymphocytes from peripheral blood, lymph nodes, a spleen or other tissues of a patient with gastric cancer. Although there is no particular restriction as to the source of the human B-cells, peripheral blood lymphocytes are preferably employed due to their easy and non-invasive availability. In order to obtain B-cells from peripheral blood the Ficoll-Hypaque density-gradient centrifugation is employed. The B-cells from lymph nodes around cancer tissue obtained in a surgical operation are suitable since they can be expected to have been sufficiently immunized with cancer-related antigens.

(2) In vitro immunization of antibody producing human B-cells

Although the antibody producing cells obtained from a patient with cancer have already been immunized by cancer-related antigen, more efficient transformation of specific antibody producing cells can be achieved by in vitro treatment, that is, by the preculture of B-cells with cancer-related antigens or B-cell mitogens.

A single cell culture of antibody producing B-cells for transformation is prepared by seeding viable B-cells in a nutrient medium with an appropriate antigen or one of the B-cell mitogens at an appropriate concentration, culturing the B-cells for a sufficient period of time and isolating viable B-cells.

Since cancer-related antigens are usually produced on the surface of cancer cell lines, the preculture of the antibody producing cells with the cancer cell lines under limited growth would be suitable for the proliferation of specific antibody producing B-cells.

Suitable B-cell mitogens which can be employed in the present invention include, for example, lipopolysaccharides of the outer cell membranes of Gram negative bacteria and pokeweed mitogen. The preculture of the antibody producing B-cells with such mitogens advantageously enriches the antibody producing B-cells.

(3) Preparation of HAT sensitive lymphoblastoid B-cell line

A HAT sensitive lymphoblastoid cell line (hereinafter "AS-1") obtained from lymphoblastoid B-cell line RPMI-1788 deposited at the American Type Culture Collection (ATCC accession number CRL 8118) is prepared. This B-cell line cannot grow in a medium containing hypoxanthine, aminopterin and thymidine (hereinafter "HAT medium").

(4) Mixed culture transformation

The suspended B-cells immunized with the cancer-related antigen or stimulated with the mitogen and AS-1 are mixed in a HAT medium containing $2\times10^{-5}$M to $5\times10^{-4}$M levamisole which is effective for acceleration of the transformation of B-cells, and the mixture is poured into each U-shaped well of microtestplates (96 wells/plate). Half of the spent medium is replaced by fresh HAT-medium every four days. Transformed cell clusters can be observed among many dead AS-1 cells or dormant lymphocytes after 20 days through an inverted microscope.

II. Establishment of B-cell Line Designated 418-59

(1) Selection of transformed B-cell line producing monoclonal antibodies reactive with gastric cancer-related antigens According to this invention, the human immunoglobulin reactive with gastric cancer cell lines in the culture supernatant is assayed by the enzyme immunoassay using a biotin-avidin system (Vector Laboratories, Inc. Burlingame, U.S.A.). Gastric cancer cell lines MKN-45, MKN-1 and Kato-III are employed as the target cells expressing gastric cancer-related antigens. These three gastric cancer cell lines are commercially available from Immuno Biological Laboratories, Fujioka-shi, Gumma-ken, Japan.

Employing the assay system the transformed B-cell culture which secretes a novel IgM having the lambda light chain has been discovered. The B-cell line cloned from this culture, designated 418-59, was deposited on July 10, 1985 at the National Collection of Animal Cell Cultures, Porton Down, Salisbury, Wiltshire, United Kingdom (Deposit ref 85071031) in accordance with the provisions of the Budapest Treaty.

The IgM produced by this B-cell line reacts with each of the gastric cancer cell lines. Besides, the IgM reacts with lung cancer cell line PC-10 which is also commercially available from Immuno Biological Laboratories, Fujioka-shi, Gumma-ken, Japan.

(2) Characteristics of antigen on cancer cell line

The molecular weight of the antigen obtained from gastric cancer cell line MKN-45 is $45\pm3$ kilodaltons determined by the polyacrylamide gel electrophoresis in the presence of sodium dodecyl sulfate (hereinafter "SDS-PAGE"), the western blotting and the immunostaining by the biotinavidin system. The isoelectric point of the antigen is $4.7\pm0.6$, determined by the isoelectric focusing electrophoresis system (LKB-Produkter AB, Bromma, Sweden).

Another antigen which shows the same molecular weight and the same isoelectric point as those of the antigen obtained from MKN-45 can also be extracted from gastric cancer cell line Kato-III.

(3) Detection of Antigen on Paraffin-embedded Tissue Samples of Gastric or Other Cancers The formalin-fixed and paraffin-embedded tissue samples of a highly or poorly differentiated gastric cancer or a lung cancer are subjected to the immunostaining with the IgM. In view of the positive results, it can be said that the antigen exists in cancer portions of some patients with gastric or lung cancer.

(4) Reactivity of IgM with human normal cells

The IgM does not react with human normal erythrocytes, leukocytes, lymphocytes or monocytes. Accordingly, the antigen is different from the known human lymphocyte antigens or blood group antigens.

III. Isolation of Antigen from MKN-45

The antigen can be isolated from the extract of MKN-45 in the presence of a suitable detergent such as Nonidet P40, Tween 20, Tween 80, Triton X-100 and other complexes of polyoxyethylene ethers of mixed partial oleic sorbitol anhydrides.

The IgM is coupled with cyanogen bromide (hereinafter "CNBr")-activated Sepharose 4B (Pharmacia Fine Chemicals AB, Uppsala, Sweden), and the resultant IgM-bound Sepharose is packed into a column. A solution containing the antigen is applied to the column, and the column is washed with a phosphate-buffered saline solution (hereinafter "PBS"). The adsorbed antigen is eluted with a glycine-HCl buffer (pH2.5) solution. The purified antigen thus obtained shows a single band with a molecular weight of $45\pm3$ kilodaltons by SDS-PAGE and an isoelectric point of $4.7\pm0.6$ by isoelectric focusing electrophoresis, which are the same as those previously determined by the immunological method.

IV. Clinical Application of IgM and Antigen

The IgM of this invention can be used for site-directed therapy. When a cytotoxic drug-conjugated human immunoglobulin is administered to gastric or lung cancer patients, the antibody would be bound to the cancer site, highly concentrating the drug in the area.

In diagnosis, the antibody would be labeled with a radioisotope or a fluorochrome reagent, the labeled antibody would be administered to a patient to localize the radioactivity at the cancer portion of the patient and to permit radiography at the target organ or the whole body.

The antigen is a new marker of cancer. Testing for the presence of the antigen in serum would be a valuable, non-invasive assay for the diagnosis of cancer.

EXAMPLE (1) Preparation of antibody producing B-cells from patient with gastric cancer A lymph node of a patient with gastric cancer diagnosed from histological observation as a signet ring cell carcinoma, was obtained from a pathological tissue sample, cut into pieces by a pair of scissors, and passed through a stainless mesh of 100 mesh to aseptically obtain a single cell suspension containing $3\times10^7$ B-cells.

(2) Preparation of HAT sensitive mutant cell line AS-1

A known human lymphoblastoid B-cell line RPMI-1788 was cultured in RPMI-1640 medium supplemented with 20% (v/v) foetal calf serum (hereinafter "FCS") and $10^{-4}$ g/ml of 8-azaguanine to isolate mutants resistant to 8-azaguanine. The azaguanine-resistant clone thus isolated was designated AS-1. Then, the AS-1 cells were routinely grown in RPMI-1640 medium supplemented with 10% to 20% (v/v) FCS. The AS-1 cells doubled in concentration every 18 hours and secreted an IgM having the lambda light chain.

(3) Mixed culturing of two kinds of cells

The two kinds of cells as prepared in procedures (1) and (2) were mixed in a HAT medium containing levamisole (RPMI-1640 of basal medium, 20% FCS, $4\times10^{-4}$M hypoxanthine, $4\times10^{-7}$M aminopterin, $1.6\times10^{-5}$M thymidine and $1\times10^{-4}$M levamisole) and then 0.1 ml of the medium containing $10^4$ cells from the lymph node and $2\times10^4$ from the AS-1 cells were poured into each well of 30 microtestplates (96 wells/plate). The microtestplates were incubated in a $CO_2$-incubator where the $CO_2$ concentration was maintained at 5% (v/v). Half of the spent medium was replaced by the HAT medium every four days, and 20 days later 115 clusters of transformed cells were observed through an inverted microscope.

(4) Selection of cell culture containing monoclonal antibody reactive with gastric cancer cell lines Step 1. $5\times10^4$ cells of gastric cancer cell line MKN-45, MKN-1 and Kato-III as the target cells were poured into each U-shaped well of a microtestplate, and 0.05 ml of the spent media from 115 wells as obtained in procedure (3) were transferred into each well containing the target cancer cells of the microtestplate, which was then gently mixed and incubated at 20° C. for one hour.

Step 2. The microtestplate was centrifuged and the supernatants were removed. Then, the microtestplate was washed once with PBS containing 0.2% (w/v) bovine serum albumin (hereinafter "PBS-ALB"), and 0.05 ml of PBS-ALB containing $5\times10^{-6}$ g/ml of a mixture (1:1) of two biotinylated antibodies (1) goat anti-human kappa chain and (2) goat anti-human lambda light chain was poured into each well of the microtestplate. After the microtestplate was gently mixed and incubated at 20° C. for 30 minutes, it was washed twice with PBS-ALB.

Step 3. 0.05 ml of PBS-ALB containing 2%.(v/v) biotinylated peroxidase-avidin complex solution (ABC Reagent; Vector Laboratories, Inc., Burlingame, U.S.A.) was poured into each well of the microtestplate, which was subsequently gently mixed and incubated at 20° C. for 30 minutes, and washed twice with PBS-ALB.

Step 4. 0.1 ml of a substrate solution for measuring peroxidase activity consisting of a tris(hydroxymethyl-)aminomethane (hereinafter "Tris")-HCl buffer (pH 7.4), 0.5 mg/ml of diaminobenzidine tetrahydrochloride and 0.02% (v/v) $H_2O_2$ was poured into each well of the microtestplate. After the reaction at 20° C. for 10 minutes, the target cancer cells were observed to have stained brown through an inverted microscope.

Consequently, 5 wells of the transformed cell culture showed positive results. Further, the evaluation of the spent media collected 5 days later was repeated, and only one transformed cell culture had reproducible reactivity with the cancer cell lines.

(5) Cloning of transformed cell culture

By the limiting dilution method, cloning of a cell culture producing an immunoglobulin reactive with gastric cancer cell lines was performed. More specifically, 0.1 ml of RPMI-1640 containing 20% (v/v) FCS, the cells (3 cells per ml) of the culture selected in Step 4 of procedure (4) and 0.1% (v/v) sheep red blood cell was poured into each well of 5 microtestplates (96 wells/plate). Cell clusters were observed after the incubation in a $CO_2$-incubator for 2 weeks, and the supernatants of the cultures were assayed using MKN-45 as the target cell line according to procedure (4). As a result, each clone from the culture produced an IgM having the lambda light chain which reacted with the surface of viable MKN-45.

Cloned cell culture, which turned to a B-cell line designated 418-59, was deposited at NCACC. The IgM produced by this cell line 418-59 reacted not only with MKN-45, but also with MKN-1, KATO-III and lung cancer cell line PC-10.

(6) Purification of antigen from MKN-45

$10^{10}$ cells of MKN-45 were mixed with 50 ml of PBS containing 1% (w/v) Nonidet P40 (nonionic detergent; Sigma Chemical, St. Louis, U.S.A.), 1 mM orthophenylenediamine, 1 mM phenylmethylsulfonyl fluoride and 1 mM ethylene diaminetetraacetic acid and then gently shaked at 4° C. for 2 hours. After the centrifugation at 1600 rpm for 10 minutes, the supernatant was collected and concentrated by the ultrafiltration system using PM-10 membrane (Amicon Corporation, Lexington, MA, USA), and washed with PBS. The final volume of the concentrated supernatant was 3 ml, and the final concentration of Nonidet P40 was estimated at about 0.01% (w/v).

The affinity-purified IgM produced by 418-59 was coupled with 1 ml of CNBr-activated Sepharose 4B (Pharmacia Fine Chemicals AB, Uppsala, Sweden). The IgM-bound Sepharose was packed into a 1 ml volume column. Then, 3 ml of the concentrated supernatant was slowly applied to the column, and the column was washed with 50 ml of PBS. The antigen adsorbed was eluted by a glycine-HCl buffer (pH 2.5).

The solution thus obtained was dialyzed against PBS containing 0.1% (w/v) NP-40. The resultant solution contained about $2 \times 10^{-5}$ g of protein which was determined by the method of Lowry et al. using bovine serum albumin as a standard. The antigen in the solution could be stained with Coomassie Brilliant Blue R-250 on SDS-PAGE plate and its molecular weight was estimated at 45±3 kilodaltons.

About $10^{-5}$ gram of the purified antigen was applied to an isoelectric focusing electrophoresis system of 110 ml scale in the presence of 0.1% (w/v) Tween 20 (nonionic detergent; Sigma Company, St. Louis, U.S.A.) using Carrier Ampholine (LKB- Produkter AB, Bromma, Sweden) whose pH range was 3.5-10. After completion of the electrophoresis, the solution was fractionated into 60 fractions and the pH of each fraction was measured, and the existence of the antigen was determined by the same method as described in III. As a result, the isoelectric point of the antigen was 4.7±0.6.

(7) Reactivity of antibody with blood cells

Heparinized adult human blood was centrifuged at 1000 rpm for 20 minutes to collect a fraction rich in erythrocytes and a fraction rich in leukocytes. Also, a fraction rich in lymphocytes and monocytes was separately collected by the specific gravity gradient centrifugation using a Ficoll-Hypaque solution at 400 G for 30 minutes. Then, these three fractions were washed twice with PBS, respectively, and $10^6$ cells of each fraction were poured into a 1 ml volume tube, respectively. After the supernatants were removed, 1 ml of the cultured medium containing $10^{-5}$ g of the monoclonal antibody was added to each of the tubes, which were then gently mixed and incubated at 20° C. for one hour to conduct the antigen-antibody reaction. The reaction mixture was centrifuged at 1000 rpm for 5 minutes and the supernatants were removed and the target cells were washed twice with PBS-ALB. Then, 1 ml of fluorescein isothiocyanate coupled with an anti-human IgM antibody produced by goat was diluted 1/10, 1/20 and 1/50, respectively, and added to each of the tubes, which were subsequently gently mixed and incubated at 20° C. for 30 minutes. After the supernatants were removed and the target cells were washed twice with PBS, the stained cells were observed through a fluorescence microscope. As a result, the monoclonal antibody did not react with any of the normal human erythrocytes, leukocytes, lymphocytes and monocytes.

The above described procedures were repeated with heparinized adult blood obtained from four healthy donors and the results were the same as described above.

We claim:

1. The human monoclonal antibody 418-59 produced by the B-cell line which has ECACC Deposit reference number 85071031 and which binds to a gastric cancer cell line.

2. The B-cell line 418-59 which has ECACC Deposit reference number 85071031 and which produces a human monoclonal antibody which binds to a gastric cancer cell line.

* * * * *